United States Patent
Eh et al.

(10) Patent No.: US 6,815,413 B2
(45) Date of Patent: Nov. 9, 2004

(54) MACROCYCLIC KETONES

(75) Inventors: Marcus Eh, Holzminden (DE); Ingo Wöhrle, Holzminden (DE)

(73) Assignee: Symrise GmbH & Co. KG (DE)

( * ) Notice: Subject to any disclaimer, the term of this patent is extended or adjusted under 35 U.S.C. 154(b) by 311 days.

(21) Appl. No.: 09/921,237

(22) Filed: Aug. 2, 2001

(65) Prior Publication Data

US 2002/0055453 A1 May 9, 2002

(30) Foreign Application Priority Data

Aug. 4, 2000 (DE) .......................................... 100 38 021

(51) Int. Cl.$^7$ ................................................ A61K 7/46
(52) U.S. Cl. ........................ 512/27; 568/303; 568/338; 568/341; 568/343; 568/347; 568/361; 568/365; 568/366
(58) Field of Search ............................ 512/27; 568/303, 568/338, 341, 343, 347, 361, 365, 366

(56) References Cited

U.S. PATENT DOCUMENTS

| | | | |
|---|---|---|---|
| 3,718,696 A | | 2/1973 | Mookherjee et al. ........ 260/586 |
| 3,923,699 A | | 12/1975 | Komatsu et al. ............ 252/522 |
| 3,935,270 A | * | 1/1976 | Calderon .................... 568/365 |
| 4,885,397 A | | 12/1989 | Bueschken ................... 568/341 |
| 5,120,880 A | * | 6/1992 | Huellmann et al. ......... 568/412 |

FOREIGN PATENT DOCUMENTS

| | | |
|---|---|---|
| DE | 532 654 | 9/1931 |
| EP | 0 025 869 | 4/1981 |

OTHER PUBLICATIONS

Fragrance Chemistry: The Science of the Sense of Smell (month unavailable) 1982 pp. 444–469, V. Synthesis of Musk Components, Braja D. Mookherjee and Richard A. Wilson.

Helv. Chem. Acta, 9, (month unavailable) 1926, pp. 230–248, Zur Kenntnis des Kohlenstoffringes I. Uber Die Konstitution des Zibetons, von L. Ruzicka.

Ernahrungs–Umschau 43 pp. 442–449 (month unavailable) 1996, Synthetische Moschusduftstoffe–Anwendung, Anreicherung in der Umwelt und Toxikologie, Gerhard Rimkus, Hubertus Brunn.

Ernahrungs–Umschau 44 pp. 4–9 (month unavailable) 1997, Synthetische Moschusduftstoffe–Anwendung, Anreicherung in der Umwelt und Toxikologie, Hubertus Brunn, Gerhard Rimkus.

* cited by examiner

Primary Examiner—Robert J. Warden, Sr.
Assistant Examiner—Monique T. Cole
(74) Attorney, Agent, or Firm—Pendorf & Cutliff

(57) ABSTRACT

Lower alkyl- and lower alkylidene-substituted, saturated or unsaturated cyclohexadecanones are grand fragrances with muscone note with which perfumes with new odor notes can be prepared.

7 Claims, No Drawings

MACROCYCLIC KETONES

FIELD OF THE INVENTION

The invention relates to novel lower alkyl- and lower alkylidene-substituted, saturated or unsaturated cyclohexadecanones, to their preparation and use in functional perfumery and in fine perfumery.

BACKGROUND OF THE INVENTION

Compounds with a musk odor are sought-after components in the perfume industry. They are characterized both by their property of imparting radiance to perfume compositions and also by their ability to act as fixatives. For this reason, musk fragrances are nowadays used in many perfume compositions.

The class of nature-similar macrocyclic musk fragrances will become more and more important in the future since the synthetic musk compounds of the nitroaromatic and polycyclic series are persistent and lipophilic, meaning that these compounds accumulate in aquatic food chains and fatty tissue (Ernährungs-Umschau 1996, 43, 442 to 449; Ernährungs-Umschau 1997, 44, 4 to 9).

Typical musk fragrances are characterized by a macrocyclic ring having 13 to 17 carbon atoms which carries a ketone or an ester as functional group. As is known, the stability of ketones in acidic and in alkaline media is greater than that of the corresponding lactones. Moreover, an alkyl substitution, preferably a methyl substitution, in the macrocyclic ring is also possible.

A preferred fragrance in perfumery is muscone.

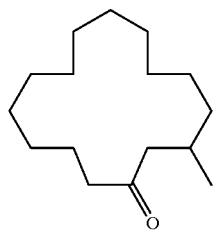

3-methylcyclopentadecanone
(muscone)

Muscone is one of the most important ingredients of the scent gland of the musk deer and, since its structural determination in 1926 (Helv. Chim. Acta, 9, 230, 1926), numerous syntheses both for racemic muscone, and also for optically pure muscone have been published (Fragrance Chemistry. The Science of the Sense of Smell, ed. E. T. Theimer, Academic Press, 1982, pages 444 to 469). The syntheses involve many reaction stages and require expensive starting materials and/or reaction components. For this reason, the amounts of expensive muscone used in functional perfumery and also in fine perfumery are limited.

SUMMARY OF THE INVENTION

There is, therefore, a pressing need for further macrocyclic compounds with muscone note which can be prepared in an efficient synthesis from cost-effective starting materials and, moreover, extend the perfumer's options with their original scent properties.

The object was therefore to find novel cost-effective macrocyclic ketones with muscone note.

We have found novel macrocyclic ketones of the general formula

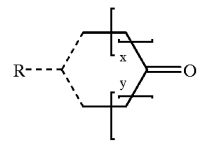

in which
R is a lower alkyl or lower alkylidene group,
x=5 and y=7, or
x=6 and y=6, and
the dashed lines are, independently of one another, a C—C single bond or a C=C double bond.

DETAILED DESCRIPTION OF THE INVENTION

Surprisingly, it has been found that the novel macrocyclic ketones have a strong and typical muscone odor. The finding is surprising in as much as the cyclohexadecanone and 8-cyclohexadecenone already known as fragrances do not smell muscone-like.

Preference is given to macrocyclic ketones of the formula

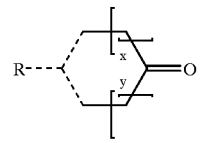

in which
R is methyl or ethyl and
x and y and the dashed lines have the meaning given above.

A lower alkyl generally means a saturated hydrocarbon radical having 1 to 6 carbon atoms. By way of example, mention may be made of: methyl, ethyl, propyl, isopropyl, butyl, isobutyl, pentyl, isopentyl, hexyl and isohexyl.

Preferred radicals are methyl and ethyl.

A most preferred radical is methyl.

A lower alkylidene generally means an unsaturated hydrocarbon radical having 1 to 6 carbon atoms, for example methylidene, ethylidene, propylidene, isopropylidene, butylidene, isobutylidene, pentylidene, isopentylidene, hexylidene and isohexylidene.

Preferred radicals are methylidene and ethylidene.

A most preferred radical is methylidene.

Specifically, the following cyclohexadecenones or cyclohexadecanones may be mentioned:
8-methylenecyclohexadecanone
9-methylenecyclohexadecanone
8-ethylenecyclohexadecanone
9-ethylenecyclohexadecanone
8-methyl-(E/Z)-7/-(E/Z)-8-cyclohexadecenone
9-methyl-(E/Z)-8-cyclohexadecenone
8-ethyl-(E/Z)-7/-(E/Z)-8-cyclohexadecenone
9-ethyl-(E/Z)-8-cyclohexadecenone
8-methylcyclohexadecanone
9-methylcyclohexadecanone
8-ethylcyclohexadecanone
9-ethylcyclohexadecanone We have found a process for the preparation of the lower alkyl- or lower alkylidene-substituted cyclohexadecenones or cyclohexadecanones according to the present invention of the formula

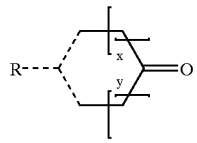

in which
the dashed lines, independently of one another, are a C—C single bond or a C=C double bond,
R is a lower alkyl or lower alkylidene group,
x=5 and y=7, or
x=6 and y=6,
which is characterized in that cyclohexadecanedione of the formula

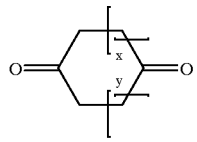

in which
x and y have the meaning given above,
and is used as starting material, in a first step, is reacted with a lower alkyltriphenylphosphonium halide and a strong base in an aprotic solvent, and the resulting lower alkylidenecyclohexadecanones are optionally isomerized and hydrogenated.

In this process, cyclohexadecanedione (J. Org. Chem., 1968, 33, 4541; U.S. Pat. No. 3,935,270) is reacted in the first process with 0.1 to 2.0 equivalents, preferably with 0.2 to 1.6 equivalents and most preferably 0.3 to 1.2 equivalents, of lower alkyl-triphenylphosphonium halide and 0.1 to 2.0 equivalents, preferably with 0.2 to 1.6 equivalents and most preferably with 0.3 to 1.2 equivalents, of a strong base (e.g. KO$^t$Bu, n-BuLi etc.) in an aprotic solvent (e.g. diethyl ether, THF, toluene, hexane etc.) under reflux (Chem. Rev., 1989, 89, 863; Synth. Commun., 1985, 15, 855). The resulting product mixture of cyclohexadecanedione, lower alkylidene-cyclohexadecanone and di-lower alkylidene-cyclohexadecane is purified (e.g. by distillation or chromatography), giving the lower alkylidene-cyclohexadecanones according to the present invention in pure form.

The new types of lower alkylidene-cyclohexadecanones synthesized by the method described above can be derivatized to give two further novel classes of compound. Firstly, the lower alkylidene-cyclohexadecanones are heated in toluene with the addition of from 0.01 to 2.0 equivalents, preferably 0.05 to 1.0 equivalents and most preferably 0.1 to 0.5 equivalents of p-toluenesulphonic acid to a temperature of from 80° C. to 110° C. and preferably 100° C. to 110° C. (Tetrahedron, 1998, 54, 865), and isomerize under these conditions to give the lower alkyl-cyclohexadecenones according to the present invention. Next, the lower alkylidene-cyclohexadecanones according to the present invention are hydrogenated under a standard hydrogen pressure at a temperature of from 25° C. to 70° C. and preferably 40° C. to 60° C. in ethyl acetate and Pd/C as hydrogenation catalyst to give the lower alkyl-cyclohexadecanones according to the present invention.

The first process according to the present invention can be illustrated using the example of 9-methylenecyclohexadecanone and subsequent products by the equation below:

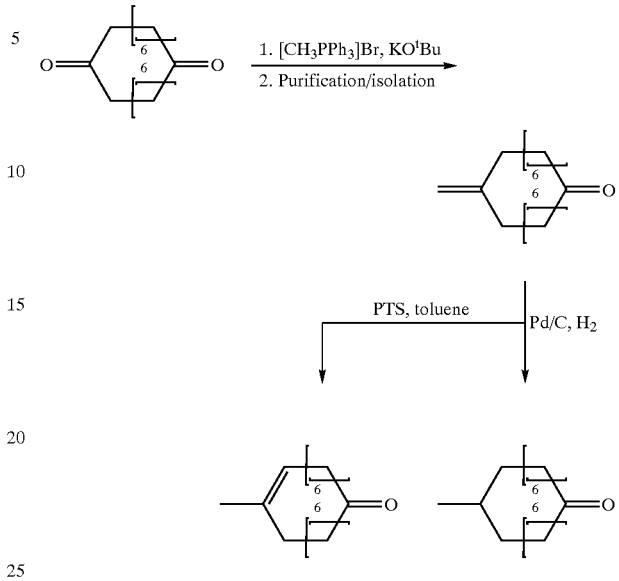

An alternative process for the preparation of the lower alkyl- or lower alkylidene-substituted cyclohexadecanones according to the invention of the formula

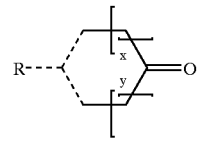

in which
the dashed lines, independently of one another, are a C—C single bond or a C=C double bond,
R is a lower alkyl or lower alkylidene group,
x=and y=7, or
x=6 and y=6,
is characterized in that, in a first step, the keto function is protected via an ethylene acetal. Subsequent Wittig reaction and deprotection produces the lower alkylidene-cyclohexadecanones, which are optionally isomerized and hydrogenated.

In the alternative process, cyclohexadecanedione (J. Org. Chem., 1968, 33, 4541; U.S. Pat. No. 3,935,270) is reacted with 0.1 to 2.0 equivalents, preferably with 0.3 to 1.5 equivalents, and most preferably with 0.8 to 1.2 equivalents, of ethylene glycol and 0.01 equivalents to 0.5 equivalents, preferably 0.05 to 0.2 equivalents of p-toluenesulphonic acid in toluene with a water separator. The resulting compound mixture of cyclohexadecanedione, dioxaspiroeicosanone and tetraoxadispirotetracosane is used as a compound mixture or also, after purification, e.g. distillation or chromatography, as pure dioxaspiroeicosanone in the subsequent Witting reaction.

The compound mixture comprising cyclohexadecanedione, dioxaspiroeicosanone and tetraoxa-dispirotetracosane obtained as in the 1st step is reacted under reflux with 0.1 to 2.0 equivalents, preferably with 0.3 to 1.5 equivalents and particularly preferably with 0.8 to 1.2 equivalents (per mole of keto function) of lower alkyltriphenylphosphonium halide and 0.1 to 2.0 equivalents, preferably 0.3 to 1.5 equivalents and particularly preferably 0.8 to 1.2 equivalents (per mole of keto function) of a strong base (e.g. KO$^t$Bu, n-BuLi etc.) in an aprotic solvent (e.g. diethyl ether, THF, toluene, hexane etc.)

The resulting product mixture, containing di-lower alkylidene-cyclohexadecane, lower alkylidene-dioxaspiroeicosane and tetraoxadispirotetracosane is purified (e.g. by chromatography or distillation), so that exclusively lower alkylidene-dioxaspiroeicosane is used in the subsequent acetal cleavage.

The lower alkylidene-dioxaspiroeicosane is reacted in a 3:1 acetone/water mixture with the addition of from 0.01 to 0.8 equivalents and preferably 0.1 to 0.5 equivalents of pyridinium p-toluenesulphonate, so that the lower alkylidene-cyclohexadecanones according to the present invention result.

The subsequent derivatizations (double-bond isomerization and double-bond hydrogenation) are carried out analogously to the descriptions of the first process.

For the case where pure dioxaspiroeicosanone is available after the first stage, this is reacted with 1.0 to 2.0 equivalents and preferably with 0.8 to 1.2 equivalents of lower alkyl-triphenylphosphonium halide and 0.8 to 1.2 equivalents and preferably 1.0 to 1.4 equivalents of a strong base (e.g. KO$^t$Bu, n-BuLi etc.) in an aprotic solvent (e.g. diethyl ether, THF, toluene, hexane etc.).

The subsequent acetal cleavage, double-bond isomerization or double-bond hydrogenation takes place in accordance with the procedures described above.

The process according to the present invention can be illustrated using the example of 9-methylenecyclohexadecanone and subsequent products by the following equation:

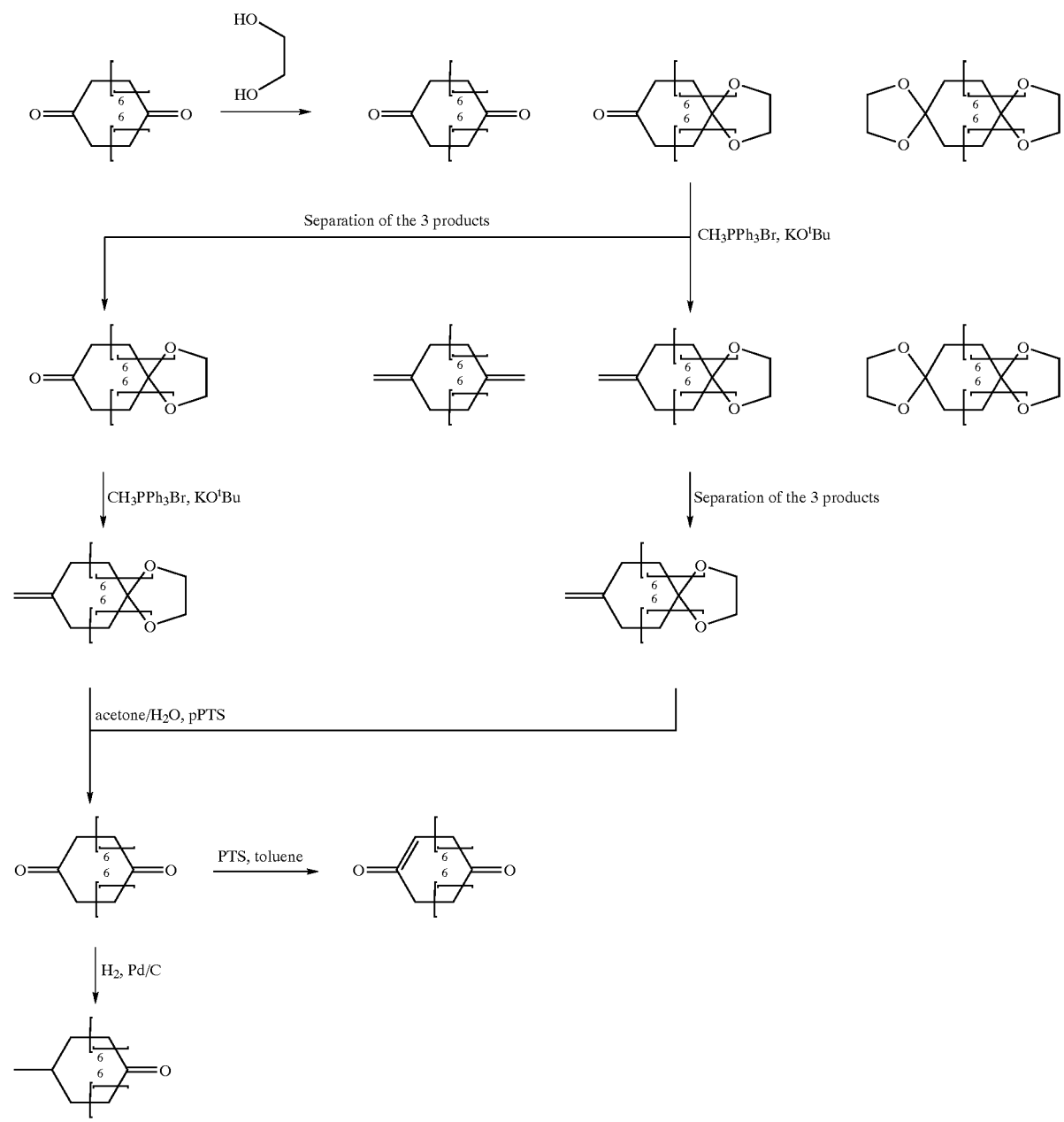

The macrocyclic ketones according to the present invention can be used as individual substances in a large number of products; they can be combined particularly advantageously with other fragrances to give new types of perfume compositions.

By using the macrocyclic ketones according to the present invention, it is generally possible, even in a low concentration, to achieve fine, erogenous musk notes, the overall odor impression being remarkably harmonized, the radiance being perceptibly increased and the fixing, i.e. the adhesive power of the perfume oil, being considerably intensified.

Examples of fragrances with which the macrocyclic ketones according to the present invention can be advantageously combined are given, for example, in S. Arctander, Perfume and Flavor Materials, Vol. I and II, Montclair, N.J., 1969, published privately or K. Bauer, D. Garbe and H. Surburg, Common Fragrance and Flavor Materials, $3^{rd}$ Ed., Wiley-VCH, Weinheim 1997.

Individual examples which may be mentioned are:
extracts from natural raw materials such as essential oils, concretes, absolutes, resins, resinoids, balsams, tinctures, such as, for example, ambergris tincture; amyris oil; angelica seed oil; angelica root oil; aniseed oil; valerian oil; basil oil; wood moss absolute; bay oil; mugwort oil; benzoin resin; bergamot oil; beeswax absolute; birch tar oil; bitter almond oil; savory oil; bucco leaf oil; cabreuva oil; cade oil; calmus oil; camphor oil; cananga oil; cardamom oil; cascarilla oil; cassia oil; cassia absolute; castoreum absolute; cedar leaf oil; cedarwood oil; cistus oil; citronella oil; lemon oil; copaiva balsam; copaiva balsam oil; coriander oil; costus root oil; cumin oil; cypress oil; davana oil; dill herb oil; dill seed oil; eau de brouts absolute; oakmoss absolute; elemi oil; estragon oil; eucalyptus citriodora oil; eucalyptus oil; fennel oil; spruce needle oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; blue camomile oil; Roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; distilled lime oil; pressed lime oil; linaloe oil; litsea cubeba oil; bayleaf oil; mace oil; marjoram oil; mandarin oil; massoi bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange-flower absolute; orange oil; origanum oil; palmarosa oil; patchouli oil; perilla oil; Peruvian balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmation sage oil; Spanish sage oil; sandalwood oil; celery seed oil; spike lavender oil; Japanese anise oil; styrax oil; tagetes oil; fir needle oil; tea-tree oil; turpentine oil; thyme oil; Tolu balsam; tonka absolute; tuberose absolute; vanilla extract; violet leaf absolute; verbena oil; vetiver oil; juniper oil; wine lees oil; absinthe oil; wintergreen oil; ylang oil; hyssop oil; civet absolute; cinnamon leaf oil; cinnamon bark oil; and fractions thereof, or ingredients isolated therefrom;
individual fragrances from the group of hydrocarbons, such as, for example, 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene;
of aliphatic alcohols, such as, for example, hexanol; octanol; 3-octanol; 2,6-dimethylheptanol; 2-methylheptanol, 2-methyloctanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol; of aliphatic aldehydes and 1,4-dioxacycloalken-2-ones thereof, such as, for example, hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethyl acetal; 1,1-dimethoxy-2,2,5-trimethyl-4-hexene; citronellyl oxyacetaldehyde;
of aliphatic ketones and oximes thereof, such as, for example, 2-heptanone; 2-octanone; 3-octanone; 2-nonanone; 5-methyl-3-heptanone; 5-methyl-3-heptanone oxime; 2,4,4,7-tetramethyl-6-octen-3-one; of aliphatic sulfur-containing compounds, such as, for example, 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;
of aliphatic nitriles, such as, for example, 2-nonenenitrile; 2-tridecenenitrile; 2,12-tridecadienenitrile; 3,7-dimethyl-2,6-octadienenitrile; 3,7-dimethyl-6-octenenitrile;
of aliphatic carboxylic acids and esters thereof, such as, for example, (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octynoate; methyl 2-nonynoate; allyl 2-isoamyloxyacetate; methyl 3,7-dimethyl-2,6-octadienoate;
of acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates, 3-methyl-2-butenoates thereof;
of acyclic terpene aldehydes and ketones, such as, for example, geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethyl acetals of geranial, neral, 7-hydroxy-3,7-dimethyloctanal;
of cyclic terpene alcohols, such as, for example, menthol; isopulegol; alpha-terpineol; terpineol-4; menthan-8-ol; menthan-1-ol; menthan-7-ol; borneol; isoborneol; linalool oxide; nopol; cedrol; ambrinol; vetiverol; guaiol; and formates, acetates, propionates, isobutyrates, butyrates, isovalerates, pentanoates, hexanoates, crotonates, tiglinates, 3-methyl-2-butenoates thereof;
of cyclic terpene aldehydes and ketones, such as, for example, menthone; isomenthone; 8-mercaptomenthan-3-one; carvone; camphor; fenchone; alpha-ionone; beta-ionone; alpha-n-methylionone; beta-n-methylionone; alphaisomethylionone; beta-isomethylionone; alpha-iron; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; alpha-sinensal; beta-sinensal; acetylated cedarwood oil (methyl cedryl ketone);

of cyclic alcohols, such as, for example, 4-tert-butylcyclohexanol; 3,3,5-trimethylcyclohexanol; 3-isocamphylcyclohexanol; 2,6,9-trimethyl-Z2,Z5,E9-cyclo dodecatrien-1 -ol; 2-isobutyl-4-methyltetrahydro-2H-pyran-4-ol;

of cycloaliphatic alcohols, such as, for example, alpha-3,3-trimethylcyclo-hexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

of cyclic and cycloaliphatic ethers, such as, for example, cineol; cedryl methyl ether; cyclododecyl methyl ether; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

of cyclic ketones, such as, for example, 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 5-cyclohexadecen-1-one; 8-cyclohexadecen-1-one; 9-cycloheptadecen-1-one; cyclopentadecanone;

of cycloaliphatic aldehydes, such as, for example, 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

of cycloaliphatic ketones, such as, for example, 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert-butyl 2,4-dimethyl-3-cyclohexen-1-yl ketone;

of esters of cyclic alcohols, such as, for example, 2-tert-butylcyclohexyl acetate; 4-tert-butylcyclohexyl acetate; 2-tert-pentylcyclohexyl acetate; 4-tert-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6- indenyl isobutyrate; 4,7-methanooctahydro-5 or 6-indenyl acetate;

of esters of cycloaliphatic carboxylic acids, such as, for example, allyl 3-cyclohexyl-propionate; allyl cyclohexyloxyacetate; methyl dihydrojasmonate; methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolan-2-acetate;

of aromatic hydrocarbons, such as, for example, styrene and diphenylmethane;

of araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

of esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate; of araliphatic ethers, such as, for example, 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaldehyde dimethyl acetal; phenylacetaldehyde glycerol acetal; 2,4,6-trimethyl-4-phenyl-1,3-dioxane; 4,4a,5,9b-tetrahydroindeno [1,2-d]-m-dioxin; 4,4a,5,9b-tetrahydro-2,4-dimethylindeno [1,2-d]-m-dioxin;

of aromatic and araliphatic aldehydes, such as, for example, benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropyl-phenyl) propanal; 2-methyl-3-(4-tert-butylphenyl)propanal; 3-(4-tert-butyl-phenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxy-phenyl) propanal; 2-methyl-3-(4-methylenedioxyphenyl)propanal;

of aromatic and araliphatic ketones, such as, for example, acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-aceto-naphthone;

of aromatic and araliphatic carboxylic acids and esters thereof, such as, for example, benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

of nitrogen-containing aromatic compounds, such as, for example, 2,4,6-trinitro-1,3-dimethyl-5-tert-butylbenzene; 3,5-dinitro-2,6-dimethyl-4-tert-butylacetophenone; cinnamonitrile; 5-phenyl-3-methyl-2-pentenenitrile; 5-phenyl-3-methylpentanenitrile; methyl anthranilate; methyl N-methylanthranilate; Schiff bases of methyl anthranilate with 7-hydroxy-3,7-dimethyloctanal; 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; indole; skatole; 2-methoxy-3-isopropylpyrazine; 2-isobutyl-3-methoxypyrazine;

of phenols, phenyl ethers and phenyl esters, such as, for example, estragole; anethole; eugenole; eugenyl methyl ether; isoeugenole; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

of heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

of lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexa-decanolide; ethylene 1,12-dodecanedioate; ethylene 1,13-tridecanedioate; coumarin; 2,3-dihydrocoumarin; octahydrocoumarin.

The perfume oils containing the macrocyclic ketones according to the present invention can be used in liquid form, neat or diluted with a solvent for perfumings. Suitable solvents for this purpose are, for example, ethanol, isopropanol, diethylene glycol monoethyl ether, glycerol, propylene glycol, 1,2-butylene glycol, dipropylene glycol, diethyl phthalate, triethyl citrate, isopropyl myristate etc.

In addition, the perfume oils comprising the macrocyclic ketones according to the present invention can be adsorbed on a carrier which serves both to distribute the fragrances finely within the product and to release them in a controlled manner during use. Such carriers can be porous inorganic materials such as light sulfate, silica gels, zeolites, gypsums, clays, clay granules, gas concrete etc. or organic materials such as woods and cellulose-based substances.

The perfume oils comprising the macrocyclic ketones according to the invention can also be microencapsulated, spray dried, in the form of inclusion complexes or in the form of extrusion products and is added in this form to the product to be perfumed.

The properties of the perfume oils modified in this way can optionally be further optimized by "coating" with suitable materials with regard to a more targeted scent release, for which purpose preference is given to using wax-like polymers, such as, for example, polyvinyl alcohol.

The microencapsulation of the perfume oils can, for example, be carried out by the "coacervation method" using capsule materials made from, for example, polyurethane-like substances or soft gelatin. The spray-dried perfume oils can, for example, be prepared by spray drying an emulsion or dispersion comprising the perfume oil, where the carriers used can be modified starches, proteins, dextrin and vegetable gums. Inclusion complexes can be prepared, for example, by introducing dispersions of the perfume oil and cyclodextrins or urea derivatives into a suitable solvent, e.g. water. Extrusion products can be obtained by melting the perfume oils with a suitable wax-like substance and by extrusion with subsequent solidification, optionally in a suitable solvent, e.g. isopropanol.

In perfume compositions, the amount of macrocyclic ketones according to the present invention used is 0.05 to 50% by weight, preferably 0.5 to 20% by weight, based on the total perfume oil.

The perfume oils comprising the macrocyclic ketones according to the invention can be used in concentrated form, in solutions or in the above-described modified form for the preparation of, for example, perfume extracts, eaux de parfum, eaux de toilette, aftershaves, eaux de cologne, pre-shave products, splash colognes and perfumed freshening wipes, and the perfuming of acidic, alkaline and neutral cleaners, such as, for example, floor cleaners, window cleaners, dishwashing detergents, bath and sanitary cleaners, scouring milk, solid and liquid WC cleaners, pulverulent and foam carpet cleaners, liquid laundry detergents, pulverulent laundry detergents, laundry pretreatment agents, such as bleaches, soaking agents and stain removers, fabric softeners, washing soaps, washing tablets, disinfectants, surface disinfectants, and of air fresheners in liquid or gel form or deposited on a solid carrier, aerosol sprays, waxes and polishes, such as furniture polishes, floor waxes, shoe creams, and bodycare compositions, such as, for example, solid and liquid soaps, shower gels, shampoos, shaving soaps, shaving foams, bath oils, cosmetic emulsions of the oil-in-water, water-in-oil and water-in-oil-in-water type, such as, for example, skin creams and lotions, face creams and lotions, sunscreen creams and lotions, aftersun creams and lotions, hand creams and lotions, foot creams and lotions, depilatory creams and lotions, aftershave creams and lotions, tanning creams and lotions, haircare products, such as, for example, hairsprays, hair gels, hairsetting lotions, hair rinses, permanent and semipermanent hair colorants, hair-shaping compositions, such as cold waves and hair-smoothing compositions, hair tonics, hair creams and lotions, deodorants and antiperspirants, such as, for example, underarm sprays, roll-ons, deodorant sticks, deodorant creams, products in decorative cosmetics, such as, for example, eyeshadows, nail varnishes, foundations, lipsticks, mascara, and of candles, lamp oils, joss-sticks, insecticides, repellents, propellants.

One important use of the macrocyclic ketones according to the invention is in the perfuming of soaps and laundry detergents because of their stability in the alkaline range. In the case of the use in laundry detergent perfumings, the macrocyclic ketones according to the invention are distinguished by a substantivity which is greater than that of fragrances used hitherto, i.e. by increased absorptive power and increased adhesion of the fragrance to the washed fibers.

The invention is further illustrated but is not intended to be limited by the following examples in which all parts and percentages are by weight unless otherwise specified.

EXAMPLES

Example 1

1,4-Dioxaspiro-[4.15]-eicosan-13-one

To a solution of 44.0 g (175 mmol) of 1,9-cyclohexadecanedione in 125 ml of toluene is added 13.1 g (210 mmol) of ethylene glycol and 500 mg (2.5 mmol) of p-toluenesulphonic acid. The mixture is then heated with a water separator until visible amounts of water are no longer eliminated. Washing with sat. NaHCO$_3$ solution is then carried out, the phases are separated, the organic phase is dried over Na$_2$SO$_4$, filtration is carried out, and the solvent is removed on a rotary evaporator. This gives 57.7 g of a solid comprising 3 components having the following GC content: 1,9-cyclohexadecanedione (33.7%); 1,4-dioxaspiro-[4.15]-eicosan-13-one (52.5%); 1,4,14,17-tetraoxadispiro-[4.7.4.7]-tetracosane (13.2%).

Both the 3-component mixture and also the 1,4-dioxaspiro-[4.15]-eicosan-13-one obtained in pure form after distillation are used in the Wittig reaction below.

Example 2

1,4-Dioxaspiro-[4.15]-eicosan-(12/13)-one

The synthesis is carried out analogously to the procedure given under Example 1, except that 1,8/1,9-cyclohexadecanedione is used as starting material. This likewise gives a 3-component mixture consisting of diketone, monoacetal and diacetal, which is used as a mixture or as pure monoacetal in the Wittig reaction.

$^1$H-NMR (200 MHz, CDCl$_3$): (ppm)=1.23–1.39 (m, 16H), 1.52–1.66 (m, 8H), 2.36–2.44 (m, 4H), 3.89–3.94 (m, 4H) $^{13}$C-NMR (50 MHz, CDl$_3$): (ppm)=22.5, 22.9, 23.0, 23.4, 27.1, 27.2, 27.5, 27.6, 27.7, 27.8, 35.1, 35.2, 41.4, 42,5, 64.3, (2C), 112.1, 212.4.

Example 3

13-Methylene-1,4-dioxaspiro-[4.15]-eicosane 89.0 g (265 mmol) of methyltriphenylphosphonium bromide are added to a suspension of 29.5 g (250 mmol) of potassium tert-butoxide in 200 ml of diethyl ether, and the mixture is then refluxed for 15 minutes. Then, at 40° C., 57.7 g of the 3-component mixture prepared under Example 1, dissolved in 20 ml of diethyl ether is added dropwise to the heterogeneous mixture. The mixture is then left to react for a further 120 minutes at 40° C. and then cooled before adding 200 ml of pentane and 300 ml of water with vigorous stirring. The phases are separated and the aqueous phase is extracted a further three times with ether. The combined organic phases are washed again with water, then dried over Na$_2$SO$_4$, filtered and freed from the solvent on a rotary evaporator. Flash-chromatographic purification (cyclohexane/EtOAc=30:1, R$_f$=0.24) gives 22.6 g (84% over 2 stages) of a colorless oil.

The synthesis starting from pure 1,4-dioxaspiro-[4.15]-eicosan-13-one is carried out analogously to the procedure described above.

Example 4

(12/13)-Methylene-1,4-dioxaspiro-[4.15]-eicosane

The synthesis is carried out analogously to the procedure described under Example 3, except that the starting material used is an isomer mixture of 1,4-dioxaspiro-[4.15]-eicosan-(12/13)-one.

$^1$H-NMR (200 MHz, CDCl$_3$): δ (ppm)=1.25–1.48 (m, 20H), 1.54–1.61 (m, 4H) δ (ppm)=1.98–2.08 (m, 4H), 3.90 (s, 2H), 3.91 (s, 2H), 4,70 (s, 2H), $^{13}$C-NMR (50 MHz, CDCl$_3$): δ (ppm)=22.7, 22.8, 26.0, 26.8, 26.9, 27.0, 27.1, 27.2, 27.5, 27.6, 35.0, 35.3, 35.5, 35.6, 64.3 (2C), 109.4, 112.2, 149.7.

Example 5

((12/13)E/Z)-(12/13)-Ethylidene-1,4-dioxaspiro-[4.15]-eicosane

The synthesis is carried out analogously to the procedure described under Example 3, except that the starting mate-rials used are an isomer mixture of 1,4-dioxaspiro-[4.15]-eicosan-(12/13)-one and ethyltriphenylphosphonium bromide.

Yield: 77% over two stages $^1$H-NMR (200 MHz, CDCl$_3$): δ (ppm)=1.25–1.44 (m, 20H), 1.50–1.64 (m, 7H), 1.90–2.09 (m, 4H), 3.91 (s, 4H), 5.15–5.28 (m, 1H). $^{13}$C-NMR (50 MHz, CDCl$_3$): δ (ppm)=13.2, 22.8, 22.9, 26.3, 26.5, 27.1, 27.3, 27.4, 27.5, 27.6, 27.7, 29.4, 35.5, 35.6, 37.3, 64.3 (2C), 112.2, 118.3, 140.4.

Example 6

9-Methylenecyclohexadecanone

Variant A 4.1 g (13.9 mmol) of 13-methylene-1,4-dioxaspiro-[4.15]-eicosane are introduced into 40 ml of acetone/water= 3:1 (v/v), and 780 mg (4.1 mmol) of pyridinium p-toluenesulphonate are added thereto. The mixture is then refluxed until the reaction is complete. Virtually all of the acetone is then removed using a rotary evaporator, and 50 ml of diethyl ether are added. The organic phase is washed once with sat. NaHCO$_3$ solution and once with sat. NaCl solution, before being dried over Na$_2$SO$_4$ and, finally, concentrated on a rotary evaporator. The crude product is then purified using flash chromatography (cyclohexane/EtOAc=25:1, R$_f$=0.24), giving 3.1 g (89%) of a colorless oil.

Variant B 1.7 g (4.7 mmol) of methyltriphenylphosphonium bromide are added to a suspension of 0.55 g (4.7 mmol) of potassium tert-butoxide and 10 ml of toluene. The mixture is then heated at 40° C. for 15 minutes and then 5.0 g (19.8 mmol) of 1,9-cyclohexadecanedione, dissolved in 10 ml of toluene, are added. The mixture is then left to react for 120 minutes at 40° C. When the reaction is complete, 10 ml of pentane and 10 ml of water are added, the phases are separated, and the aqueous phase is extracted three times with diethyl ether. The combined organic phases are washed again with water, dried over Na$_2$SO$_4$, filtered off and freed from solvent on a rotary evaporator. The 3-component mixture is separated using flash chromatography (cyclohexane/EtOAc=25:1, R$_f$=0.24), giving 880 mg (75% based on methyltriphenylphosphonium bromide used) of 9-methylenecyclohexadecanone.

Odor: musk, erogenous, animalic, ambergris, pleasant muscone note, musk tincture $^1$H-NMR (200 MHz, CDCl$_3$): δ (ppm)=1.20–1.35 (m, 12H), 1.41 (quint, J=7.2 Hz, 4H), 1.63 (quint, J=6.5 Hz, 4H), 2.0 (t, J=7.2 Hz, 4H), 2.40 (dd, J=6.5 Hz, 4H), 4.70 (quint, J=0.9 Hz, 2H). $^{13}$C-NMR (50 MHz, CDCl$_3$): δ (ppm)=23.7 (2C), 26.4 (2C), 27.6 (2C), 27.8 (2C), 27.9 (2C), 35.3 (2C), 42.2 (2C), 109.8, 149.5, 212.5.

Example 7

(8/9)-Methylenecyclohexadecanone

Starting from 1,8/1,9-cyclohexadecanedione and 12/13-methylene-1,4-dioxaspiro-[4.15]-eicosane, the syntheses are carried out analogously to variants A and B given under Example 6.

Odor: musk, erogenous, animalic, ambergris, pleasant muscone note, musk tincture Data for 8-methylenecyclohexadecanone:

$^1$H-NMR (200 MHz, CDCl$_3$): δ (ppm)=1.23–1.35 (m, 12H), 1.36–1.48 (m, 4H), 1.57–1.70 (m, 4H), 2.0 (t, J=7.5 Hz, 4H), 2.37–2.44 (m, 4H), 4.69 (s, 2H). $^{13}$C-NMR (50 MHz, CDCl$_3$): δ (ppm)=23.4, 23.6, 26.4, 26.5, 27.2, 27.3, 27.5, 27.7 (2C), 27.9, 34.8, 35.3, 41.6 (2C), 109.5, 149.5, 212.4.

Example 8

(8/9)-Ethylidenecyclohexadecanone

The synthesis is carried out with ((12/13)E/Z)-(12/13)-ethylidene-1,4-dioxaspiro-[4.15]-eicosane analogously to variant A given under Example 6.
Odor: weak musk
Data for 9-ethylidenecyclohexadecanone:
$^1$H-NMR (200 MHz, CDCl$_3$): δ (ppm)=1.20–1.44 (m, 16H), 1.55 (d, J=9.1 Hz, 3H), 1.60–1.75 (m, 4H), 1.85–1.95 (m, 4H), 1.90–2.05 (m, 4H), 5.20 (q, J=6.8 Hz,1H). $^{13}$C-NMR (50 MHz, CDCl$_3$): δ (ppm)=13.2, 23.8, 23.9, 26.8, 27.1, 27.8, 27.9 (2C), 28.0, 28.1, 28.2, 29.7, 37.4, 42.2, 42.5, 118.9, 140.0, 212.6.

Example 9

9-Methyl-8(E/Z)-cyclohexadecenone 1.3 g (5.1 mmol) of 9-methylenecyclohexadecanone are introduced into 80 ml of toluene, and 145 mg (0.75 mmol) of p-toluenesulphonic acid are added thereto. The mixture is then heated at 100° C. for 44 h, then left to cool, and the organic phase is washed with sat. NaHCO$_3$ solution. The aqueous phase is then extracted three times with diethyl ether before the combined organic phases are dried over Na$_2$SO$_4$, filtered and freed from solvent. The crude product is purified by flash chromatography (cyclohexane/EtOAc= 25:1, R$_f$=0.23), giving 1.25 g (89%) of a colorless oil.
Odor: musk, erogenous, animalic, pleasant muscone note, musk tincture.
Data for the excess isomer:
$^1$H-NMR (200 MHz, CDCl$_3$): δ (ppm)=1.10–1.48 (m, 14H), 1.53 (s, 3H), 1.57–1.72 (m, 4H), 1.92–2.08 (m, 4H), 2.30–2.46 (m, 4H), 5.11 (t, J=7.6 Hz, 1H). $^{13}$C-NMR (50 MHz, CDCl$_3$): δ (ppm)=22.9, 23.4, 23.9, 26.0, 26.7, 27.1, 27.2, 27.5, 28.0, 28.1, 28.3, 38.5, 40.0, 42.5, 125.7, 134.5, 212.7.

Example 10

8-Methyl-(E/Z)-7/-(E/Z)-8-cyclohexadecenone/9-methyl-(E/Z)-8-cyclohexadecenone The synthesis proceeds analogously to the procedure described under Example 9, except that the starting material used is (8/9)-methylenecyclohexadecanone.
Odor: musk, erogenous, animalic, pleasant muscone note, musk tincture.
Data for the excess isomer:
$^1$H-NMR (200 MHz, CDCl$_3$): δ (ppm)=1.12–1.46 (m, 12H), 1.54 (s, 3H), 1.58–1.71 (m, 4H), 1.90–2.08 (m, 4H), 2.31–2.46 (m, 4H), 5.0–5.17 (m, 1H). $^{13}$C-NMR (50 MHz, CDCl$_3$): δ (ppm)=15.3, 22.9, 23.9, 26.7, 27.1, 27.2, 27.5, 28.0, 28.1 (2C), 28.3, 38.5, 40.0, 42.5, 125.8, 134.5, 212.7.

Example 11

8-Ethyl-(E/Z)-7/-(E/Z)-8-cyclohexadecenone/9-ethyl-(E/Z)-8-cyclohexadecenone The synthesis proceeds analogously to the procedure described under Example 9, except that the starting material used is (8/9)-ethylidenecyclohexadecanone.
Odor: weakly musk
Data for the excess isomer:
$^1$H-NMR (200 MHz, CDCl$_3$): δ (ppm)=0.96 (t, J=8.1 Hz, 3H), 1.14–1.44 (m, 14H), 1.54–1.72 (m, 4H), 1.91–2.10 (m, 6H), 2.22–2.47 (m, 4H), 4.95–5.27 (m,1H). $^{13}$C-NMR (50 MHz, CDCl$_3$): δ (ppm)=12.9, 23.1, 24.1, 27.4, 27.5, 27.7, 27.8, 28.0, 28.1, 28.3, 29.4, 29.6, 37.4, 40.9, 43.1, 123.6, 141.0, 212.8.

Example 12

9-Methylcyclohexadecanone 500 mg (2 mmol) of 9-methylenecyclohexadecanone are introduced into 25 ml of ethyl acetate, and 25 mg of Pd/C are added thereto. Hydrogenation is then carried out at 40° C. and standard hydrogen pressure for 5 h. When the reaction is complete, the mixture is filtered over Celite, and the crude product is freed from solvent. Purification by flash chromatography (cyclohexane/EtOAc=25:1) gives 475 mg (94%) of a colorless oil.
Odor: musk, erogenous, animalic, weak.
$^1$H-NMR (200 MHz, CDCl$_3$): δ (ppm)=0.84 (d, J=7.2 Hz, 3H), 1.06–1.18 (m, 2H), 1.20–1.36 (m, 18H), 1.39–1.49 (m, 1H), 1.55–1.64 (m, 2H), 1.64–1.74 (m, 2H), 2.34 (ddd, J=16.0, 7.8, 6.0 Hz, 2H), 2.48 (ddd, J=16.0, 7.6, 6.0 Hz, 2H). $^{13}$C-NMR (50 MHz, CDCl$_3$): δ (ppm)=21.0, 23.5 (2C), 24.6 (2C), 27.5 (2C), 27.6 (2C), 27.7 (2C), 30.6, 34.4 (2C), 42.1 (2C), 212.5.

Example 13

(8/9)-Methylcyclohexadecanone

The synthesis proceeds analogously to the procedure described under Example 12, except that the starting material used is (8/9)-methylenecyclohexadecanone.
Odor: musk, erogenous, weak.
Data for the 8-methylcyclohexadecanone isomer
$^1$H-NMR (200 MHz, CDCl$_3$): δ (ppm)=0.84 (d, J=7.2 Hz, 3H), 1.08–1.18 (m, 2H), 1.18–1.36 (m, 18H), 1.40–1.50 (m, 1H), 1.55–1.74 (m, 4H), 2.30–2.50 (m, 4H). $^3$C-NMR (50 MHz, CDCl$_3$): δ (ppm)=20.7, 23.3, 23.6, 24.6, 24.8, 27.2, 27.3, 27.4 (2C), 27.7, 27.8, 30.4, 34.0 (2C), 41.9, 42.0, 212.4.

Example 14

(8/9)-Ethylcyclohexadecanone

The synthesis proceeds analogously to the specification described under Example 12, except that the starting material used is (8/9)-ethylenecyclohexadecanone.
Odor: weakly musk
Data for the 9-ethylcyclohexadecanone isomer:
$^1$H-NMR (200 MHz, CDCl$_3$): δ (ppm)=0.84 (t, J=8.0 Hz, 3H), 1.14–1.38 (m, 23H), 1.52–1.74 (m, 4H), 2.30–2.51 (m, 4H). $^{13}$C-NMR (50 MHz, CDCl$_3$): δ (ppm)=11.6, 23.2, 23.6 (2C), 24.6 (2C), 27.6 (2C), 27.8 (2C), 27.9 (2C), 31.7 (2C), 37.9, 42.3 (2C), 212.6.

Example 15

The present perfume oil is used for the perfuming of a great variety of cosmetic products.
Composition

TABLE 1

| Ingredients | Parts by weight |
| --- | --- |
| 1. Citrophoral Base (H & R) | 5.0 |
| 2. Aldehyde C10 10% in BA | 5.0 |
| 3. Aldehyde C11 MOA 10% in BA | 3.0 |
| 4. Farenal (H & R) | 3.0 |
| 5. Aldehyde C11 10% in IPM | 5.0 |
| 6. Citroxal 50% in DEP | 2.0 |
| 7. trans Hex-2-enol 10% in BA | 2.0 |

TABLE 1-continued

| Ingredients | Parts by weight |
|---|---|
| 8. Vertocitral (H & R) | 1.0 |
| 9. Linalyl acetate | 45.0 |
| 10. Citrylal (H & R) | 5.0 |
| 11. Mandarinal (Firmenich) | 4.0 |
| 12. Lilial (Givaudan Roure) | 75.0 |
| 13. Lyral (IFF) | 75.0 |
| 14. Profarnesol (H & R) | 5.0 |
| 15. Nerolidol | 5.0 |
| 16. Linalool | 45.0 |
| 17. Geranium oil, African | 5.0 |
| 18. Phenylethyl alcohol | 75.0 |
| 19. Geraniol | 15.0 |
| 20. Nerol | 10.0 |
| 21. Hexylcinnamaldehyde, alpha | 50.0 |
| 22. Methyl dihydrojasmonate | 15.0 |
| 23. Benzyl salicylate | 100.0 |
| 24. trans,cis-2-Nonadienol 0.1% in IPM | 5.0 |
| 25. Allyl ionone (Givaudan Roure) | 3.0 |
| 26. Isomethyl ionone, gamma | 75.0 |
| 27. Eugenol | 7.0 |
| 28. Cedryl acetate | 40.0 |
| 29. Sandolen (H & R) | 5.0 |
| 30. Citral | 5.0 |

BA = benzyl alcohol;
IPM = isopropyl myristate;
DEP = diethyl phthalate

The addition of a) 355 parts by weight of 8/9-methylenecyclohexadecanone (total 1000 parts by weight) leads to a significantly perceptible harmonization of the fresh top note with the rosy-floral middle note. Moreover, with 8/9-methylenecyclohexadecanone, effects reminiscent of nitromusk are achieved and the fine erogenous musk note imparts excellent radiance and increased adhesion to the present composition. In this connection, the grand character of 8/9-methylenecyclohexadecanone in particular predominates compared with compositions containing conventional musk fragrances.

b) 55 parts by weight of 9-methyl-8(E/Z)-cyclohexadecenone (sum 700 parts by weight) impart to the composition an animalic musk note which is not achieved with existing musk fragrances. In addition, the overall composition acquires body and appears grander.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Macrocyclic ketones of the general formula

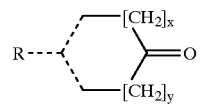

in which
R is a lower alkyl or lower alkylidene group,
x=5 and y=7, or
x=6 and y=6, and
the dashed lines are, independently of one another, a C—C single bond or a C═C double bond.

2. Macrocyclic ketones according to claim 1 of the formula

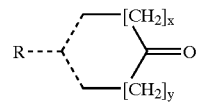

in which
R is methyl or ethyl.

3. A macrocyclic ketone according to claim 1, wherein said macrocyclic ketone is 8-Methylenecyclohexadecanone, 9-methylenecyclohexadecanone, 8-ethylenecyclohexadecanone, 9-ethylenecyclohexadecanone, 8-methyl-(E/Z)-7/-(E/Z)-8-cyclohexa-decenone, 9-methyl-(E/Z)-8-cyclohexadecenone, 8-ethyl-(E/Z)-7/-(E/Z)-8-cyclohexadecenone, 9-ethyl-(E/Z)-8-cyclohexadecenone, 8-methylcyclohexadecanone, 9-methylcyclohexadecanone, 8-ethylcyclo-hexadecanone or 9-ethylcyclohexadecanone.

4. Fragrance compositions comprising macrocyclic ketones of the general formula

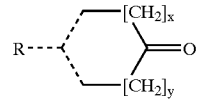

in which
R is a lower alkyl or lower alkylidene group,
x=5 and y=7, or
x=6 and y=6, and
the dashed lines are, independently of one another, a C—C single bond or a C═C double bond.

5. A fragrance composition according to claim 4, wherein said fragrance has a muscone note.

6. A process for the preparation of the lower alkyl or lower alkylidene substituted cyclohexadecenones or cyclohexadecanones of the formula

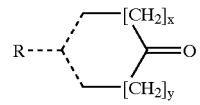

in which
the dashed lines, independently of one another, are a C—C single bond or a C═C double bond,
R is a lower alkyl or lower alkylidene group,
x=5 and y=7, or
x=6 and y=6,
wherein a cyclohexadecanedione of the formula

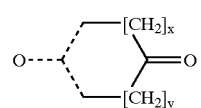

in which
x and y have the meaning given above,
is used as starting material, and in a first step is reacted with a lower alkyltriphenyiphosphonium halide and a strong base in an aprotic solvent, and the resulting lower alkylidene-cyclohexadecanones are optionally isomerized and hydrogenated.

7. A process for the preparation of lower alkyl or lower alkylidene-substituted cyclohexadecanones of the formula

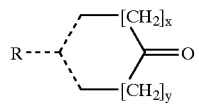

in which the dashed lines, independently of one another, are a C—C single bond or a C=C double bond, R is a lower alkyl or lower alkylidene group, x=5 and y=7, or x=6 and y=6, wherein, in a first step, a keto function of said cyclohexadecanones is protected via an ethylene acetal, then a Wittig reaction is carried out and the protective group is cleaved off and, in further steps, an isomerization and hydrogenation is optionally carried out.

* * * * *